United States Patent [19]

Hosokawa et al.

[11] Patent Number: 4,812,486

[45] Date of Patent: Mar. 14, 1989

[54] ABSORBENT RESIN WITH EXCELLENT STABILITY

[75] Inventors: Yasunori Hosokawa, Funabashi; Takatoshi Kobayashi, Utsunomiya, both of Japan

[73] Assignee: Kao Corporation, Tokyo, Japan

[21] Appl. No.: 86,476

[22] Filed: Aug. 18, 1987

[30] Foreign Application Priority Data

Aug. 22, 1986 [JP] Japan ................................ 61-196874

[51] Int. Cl.$^4$ ............................................. C08L 77/00
[52] U.S. Cl. ..................................... 521/139; 523/130; 523/200; 523/206; 523/423; 523/426; 424/418; 424/419; 424/486; 424/487; 424/488; 502/402; 502/403; 502/404

[58] Field of Search ............... 424/418, 419, 486, 487, 424/488; 523/130, 200, 206, 423, 426; 502/402, 403, 404; 521/139

[56] References Cited

U.S. PATENT DOCUMENTS 4,664,857  5/1987  Nambu ................................... 264/28

Primary Examiner—John Kight
Assistant Examiner—Samuel A. Acquah
Attorney, Agent, or Firm—Birch, Stewart, Kolasch & Birch

[57] ABSTRACT

An absorbent composition having excellent stability comprising an absorbent resin and 0.01 to 30 percent by weight, based on the dried weight of said absorbent resin, of a radical chain terminator.

9 Claims, No Drawings

ABSORBENT RESIN WITH EXCELLENT STABILITY

The present invention concerns an absorbent resin capable of rapidly absorbing a large amount of aqueous liquid and having excellent stability in a swollen state.

More particularly, the present invention relates to an absorbent resin of excellent stability capable of retaining a swollen gel state formed after absorbing aqueous liquid for a long period of time, under the usual conditions of use.

BACKGROUND OF THE INVENTION

Absorbent resins which are excellent in water absorbability and retainability and are capable of absorbing and retaining a large amount of water have been developed in recent years and utilized generally as sanitary napkins or disposable diapers in the field of sanitary goods, water retaining agents, etc., in the agricultural and horticultural fields, as well as sludge coagulants, dewing inhibitors, water stoppers, etc., in the civil engineering and constructing fields.

For such absorbent resins, there have been proposed, for example, hydrolyzate of starch-acrylonitrile graft polymers, starch-acrylic acid graft polymers, hydrolyzate of vinyl acetate-acrylate ester copolymers, crosslinking products of polyacrylic acid salts, carboxymethylcellulose, etc.

Generally, the performance of an absorbent resin is evaluated based on the absorption amount, absorption rate, gel strength in a swollen state, etc. Among them, there have been made various proposals for the improvement of the absorption performance such as the absorption amount and the absorption rate (for example, reference is made to Japanese Patent Application Laying Open Nos. Sho 57-158210, Sho 59-62665, Sho 61-97301, etc). While on the other hand, the gel strength upon swelling has an inverse relationship with the absorption amounts thus showing a trend in which the absorption amount is lowered as the strength is increased. It is considered that an ideal absorbent resin should be capable of satisfying both the absorption performance and the gel strength upon swelling as described above, but at the present time, no such resin has yet been obtained.

When the absorbent resin is swollen into a gel-like state upon absorbing water, there are problems in that it suffers from dynamic forces such as swelling pressure, as well as the gel-like resin being degraded due to circumstantial factors such as exposure to high temperature or sunlight and, further, due to the effect of oxygen in the air. In an extreme case, the swollen gel-like state can be maintained only within several hours and the function of water absorbability and retainability is lost. Similar degradation also occurs in the absorbent resin swollen by the absorption of urine, failing to retain the state of the swollen gel depending on the case. Such a phenomenon causes significant trouble upon using the absorbent resin in various application uses and the development for an absorbent resin of excellent aging stability for swollen gel has been demanded.

DESCRIPTION OF THE INVENTION

The present inventors have made extensive studies for overcoming the foregoing problems and obtaining an adsorbent resin with excellent gel strength upon swelling and aging stability of swollen gel and, as a result, have accomplished the present invention.

Specifically, the present invention provides an absorbent resin with excellent stability in which from 0.01 to 30% by weight of a radical chain terminator is incorporated to the absorbent resin.

The present invention provides an absorbent composition which has an excellent stability and comprises an absorbent resin and 0.01 to 30 percent by weight, based on the dried weight of the absorbent resin, of a radical chain terminator.

It is preferable that the absorbent resin is a crosslinked product of a salt of polyacrylic acid.

The present invention will now be described below specifically.

The absorbent resin preferably usable in the present invention can include, for example, hydrolyzate of starch-acrylonitrile polymer, starch-acrylic acid graft polymer, hydrolyzate of vinyl acetate-acrylate copolymer, crosslinking product of polyacrylic acid salt, crosslinking product of isobutylene-maleic anhydride copolymer and carboxymethylcellulose. Most preferred are the crosslinking product of polyacrylic acid salt from a view point of water absorbing performance, and there are no particular restrictions for the polymerizing process or copolymer ingredients.

Any of radical chain terminators may be used in the present invention as long as the compound has a radical chain terminating function and there can be mentioned, for example, known antioxidants, polymerization terminators, radical scavengers, etc. Among the radical chain terminators, those which are soluble by more than 0.1 g to 100 g of water at 25° C. are particularly preferred.

For example, there can be mentioned, for example, hydroquinone, p-methoxyphenol, benzoquinone, methyl hydroquinone, t-butylhydroquinone, pyrogallol, gallic acid, methyl gallate, ethyl gallate, propyl gallate, tannic acid and salts thereof such as hydrolyzed type tannin obtained from gall, etc., condensated type tannin obtained from gambier, lignin sulfonate, flavonoids such as quercetin and ellagic acid and salts thereof, phenol compounds such as cathecol, resorcinol and derivatives thereof, and amine compounds such as N-nitrosophenyl hydroxyamine ammonium salt, thiourea, etc., with no particular restrictions thereto. Among them, most preferred are pyrrogallol, gallic acid, gallic acid ester, tannic acid, flavonoids and thiourea. They may be used individually or may be used in a combination of two or more of them. Further, it is also possible to use a metal chelating agent such as phosphoric acid and citric acid or a chain transfer agent such as mercaptans, lower aliphatic alcohol or carboxylic acid together.

The content of the chain terminator in the present invention is from 0.01 to 30% by weight based on the dried weight of the absorbent resin. If the content is less than 0.01% by weight, no sufficient effect can be obtained for the improvement of the stability against light and heat, oxidation by oxygen, etc. While on the other hand, if it exceeds 30% by weight, the absorbing performance is reduced failing to obtain the purpose of the present invention. The method and the time for adding the radical chain terminator has no particular restriction so long as no hindrance is caused to the production of the resin and can be incorporated by adding during or after the production step of the absorbent resin as a solution of a solvent, preferably, water capable of dissolving them, followed by mixing and drying.

In this way, in the absorbent resin incorporated with a specified amount of the radical chain terminator, the stability of the swollen gel form after water absorption is remarkably improved and the state can be maintained over a long period of time. This supposedly, is due to the radical chain terminator which present inside the swollen gel of the resin being capable of effectively capturing the radicals, if formed due to the effect of light, heat, oxygen, etc., thereby preventing the occurrence of undesirable reaction such as decomposition and disconnection of the resin.

The absorbent resin according to the present invention is excellent in water absorbing performance and, moreover, its stability for the gel form upon swelling is satisfactory even under the effects of light, heat, etc. Accordingly, it can be used suitably for such applications, for example, as water retaining agents in the agricultural and horticultural fields, water stoppers and dewatering agents in the civil engineering and construction fields and as the absorbent material for sanitary goods such as sanitary napkins or disposal diapers.

EXAMPLE

The present invention will now be explained specifically referring to synthesis examples, examples and comparative examples. It should, however, be noted that the present invention is no way limited only to these examples.

The water absoption amount in the examples and the comparative examples are defined as such a value determined by the following procedures.

Specifically, the water absorption amount is such a value obtained by dispersing about 1 g of a resin in a large excess of physiological saline, swelling the resin sufficiently, filtering it through a 80 mesh metal screen, measuring the weight of the swollen resin (W) obtained and dividing the measured value with the weight of the unswollen resin, that is, the initial resin weight (Wo).

That is: absorption amount (g/g)=W/Wo.

Further, the water absorbing rate is represented by the amount of the physiological saline absorbed per 1 g of the resin in 20 minutes.

While on the other hand, the stability of the swollen gel is evaluated regarding light and heat as described below.

(Evaluation for Light-Fastness)

A resin swollen to an equilibrium saturation with ion exchanged water is placed in a glass bottle and applied with an irradiation test by a weatherometer (WEL-SUN-DC-B type, manufactured by Suga Shikenki Co.), and the state of the gel is observed with the passage of time.

(Evaluation for the Heat Resistance)

A resin swollen to the equilibrium saturation with ion exchanged water is placed in a glass bottle and the state of the gel is observed in a bath heated to 80° C. during days.

The scale for the evaluation of the heat resistance and the light-fastness comprises the following three steps:

o—The swollen particles retain the shape as they are.

Δ—The shape of the swollen particles becomes obscure although the particles are not dissolved.

x—The swollen particles are partially dissolved in which a liquid state is observed.

SYNTHESIS EXAMPLE 1 (Synthesis of Absorbent Resins (I), (II))

To a 2 liter-volume, four-necked, round bottom flask equipped with a stirrer, a reflux condenser, a dropping funnel and an inlet tube for nitrogen gas, 1150 ml of cyclohexane and 9.0 g of ethyl cellulose N-200, available from Hercules Inc., were charged, dissolved oxygen is purged by blowing nitrogen gas and the temperature is increased to 75° C.

Separately, 150 g of acrylic acid is neutralized with 65.8 g of an aqueous 98% sodium hydroxide solution dissolved in 200 g of ion exchanged water in a flask while applying external cooling. Then, after adding and dissolving 0.33 g of potassium persulfate and 0.015 g of N,N'-methylenebisacryl amide, they are transferred to the dropping funnel. The content is dropped to the four-necked flask for one hour. The reaction is continued for one hour while maintaining the temperature at 75° C. also after the completion of the dropping. The hydrous absorbent resin dispersed in the solvent is referred to as an absorbent resin (I).

Then, cyclohexane is distilled off under a reduced pressure and the remaining hydrous absorbent resin is dried under a reduced pressure to obtain a powdery absorbent resin (II).

SYNTHESIS EXAMPLE 2 (Synthesis of Absorbing Resin (III))

Synthesis and drying are conducted by the procedures in accordance with Synthesis Example 1 except for using 0.038 g of Denacol EX-810 (ethylene glycol diglycidyl ether, manufactured by Nagase Sangyo Co.) instead of N,N'-methylenebisacryl amide in Synthesis Example 1, to obtain an absorbent resin (III).

SYNTHESIS EXAMPLE 3 (Synthesis of Absorbent Resin (IV))

Synthesis and drying are conducted by the procedures in accordance with Synthesis Example 2 except for increasing the addition amount of Denacol Ex-810 in Synthesis Example 2 to 0.15 g, to obtain an absorbent resin (IV).

EXAMPLES 1, 2

Each 100 g of the absorbent resin (I) (Example 1) and (II) (Example 2) (based on the dried weight of the absorbent resin (I)) is placed in a cylinder twine-shell kneader and sprayed with an aqueous solution of 0.1 g of propyl gallate dissolved in 100 g of water under stirring. Then, each of the resins is dried under a reduced pressure.

EXAMPLE 3

The absorbent resin (III) is placed in an amount of 100 g to a twine-shell kneader, and a solution of 0.01 g of pyrogallol and 0.01 g of p-methoxyphenyl dissolved in 100 g of ethanol is added and stirred. Then, the resin is dried under a reduced pressure.

EXAMPLE 4

The absorbent resin (I) is placed in an amount of 100 g (based on the dry weight) into a twine-shell kneader and an aqueous solution of 15 g of tannic acid dissolved in 100 g of water is added dropwise. Then, the resin is dried under a reduced pressure.

EXAMPLE 5

The absorbent resin (II) is placed in an amount of 100 g into a twine-shell kneader, and an aqueous solution of 0.5 g of thiourea dissolved in 100 g of water is sprayed. Then, the resin is dried under a reduced pressure.

COMPARATIVE EXAMPLES 1, 2, 3

Absorbent resins (II), (III), (IV) not incorporated with the radical chain terminator are used as Comparative Examples.

Absorbent performance (absorbing amount, absorbing rate) and stability are evaluated for absorbent resins of Examples 1-5 and Comparative Examples 1-3. The results are shown in Table 1.

TABLE 1

|  |  | Water absorbing property | | Light fastbess (hr) | | | | Heat resistance (day) | | | |
| --- | --- | --- | --- | --- | --- | --- | --- | --- | --- | --- | --- |
|  |  | Absorbing amount (g/g) | Absorbing rate (ml/g. 20 min) | 1 | 2 | 5 | 10 | 1 | 5 | 10 | 20 |
| Example | 1 | 62 | 27 | o | o | o | o | o | o | o | o |
|  | 2 | 60 | 26 | o | o | o | o | o | o | o | o |
|  | 3 | 54 | 29 | o | o | o | o | o | o | o | o |
|  | 4 | 60 | 28 | o | o | o | o | o | o | o | o |
|  | 5 | 66 | 27 | o | o | o | o | o | o | o | o |
| Comparative | 1 | 60 | 27 | Δ | x | x | x | o | Δ | x | x |
| Example | 2 | 53 | 28 | o | Δ | x | x | o | o | Δ | x |
|  | 3 | 41 | 25 | o | Δ | Δ | x | o | o | Δ | Δ |

What is claimed is:

1. An absorbent composition having excellent stability comprising an absorbent resin and 0.01 to 30 percent by weight, based on the dried weight of said absorbent resin, of a radical chain terminator.

2. The composition as claimed in claim 1, in which said radical chain terminator is soluble in an amount of 0.1 gram or larger in 100 grams of water at 25° C.

3. The composition as claimed in claim 1, in which said absorbent resin is a crosslinked product of a salt of polyacrylic acid.

4. The composition as claimed in claim 1, in which said absorbent resin is a hydrolyzate of starch-acrylonitrile polymer, a starch-acrylic acid graft polymer, a hydrolyzate of vinyl acetate-acrylate copolymer, crosslinking product of polyacrylic acid salt, a crosslinking product of isobutylene-maleic anhydride copolymer and carboxymethylcellulose.

5. The composition as claimed in claim 1, in which said radical chain terminator is hydroquinone, p-methoxyphenol, benzoquinone, methyl hydroquinone, t-butylhydroquinone, pyrogallol, gallic acid, methyl gallate, ethyl gallate, propyl gallate, tannic acid or salts thereof.

6. The composition as claimed in claim 1, comprising a metal chelating agent.

7. The composition as claimed in claim 6, in which the metal chelating agent is phosphoric acid or citric acid.

8. The composition as claimed in claim 1, comprising a chain transfer agent.

9. The composition of claim 8, in which the chain transfer agent is a mercaptan, a lower aliphatic alcohol or a carboxylic acid.

* * * * *